United States Patent
Berci et al.

(10) Patent No.: US 6,743,166 B2
(45) Date of Patent: Jun. 1, 2004

(54) APPARATUS FOR INTRODUCING AN INTUBATION TUBE INTO THE TRACHEA

(75) Inventors: George Berci, Los Angeles, CA (US); Markus Lipp, Mainz (DE), by Monika Daublander, legal representative; Christian Pradel, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/928,588

(22) Filed: Aug. 13, 2001

(65) Prior Publication Data

US 2002/0072652 A1 Jun. 13, 2002

Related U.S. Application Data

(63) Continuation of application No. PCT/EP00/01138, filed on Feb. 11, 2000.

(30) Foreign Application Priority Data

Feb. 12, 1999 (DE) .......................... 199 05 840
Aug. 24, 1999 (DE) .......................... 199 39 971

(51) Int. Cl.⁷ ................................. A61B 1/00
(52) U.S. Cl. .............. 600/120; 600/130; 600/136
(58) Field of Search ..................... 600/120, 121, 600/194, 114, 130, 104, 136

(56) References Cited

U.S. PATENT DOCUMENTS

| | | | |
|---|---|---|---|
| 3,822,697 A | | 7/1974 | Komiya .................... 128/3 |
| 4,254,762 A | | 3/1981 | Yoon ..................... 128/4 |
| 4,449,532 A | * | 5/1984 | Storz .................... 606/191 |
| 4,896,986 A | * | 1/1990 | Terayama ............... 403/14 |
| 5,327,881 A | * | 7/1994 | Greene .................. 600/120 |
| 5,329,940 A | * | 7/1994 | Adair ................ 128/200.26 |
| 5,379,755 A | | 1/1995 | Heckele .................. 128/4 |
| 5,514,091 A | * | 5/1996 | Yoon ................... 604/103.11 |
| 5,733,242 A | * | 3/1998 | Rayburn et al. ......... 600/120 |
| 5,740,791 A | | 4/1998 | Aves .................. 128/200.26 |
| 5,782,748 A | * | 7/1998 | Palmer et al. .......... 600/104 |
| 5,807,237 A | * | 9/1998 | Tindel .................. 600/114 |

FOREIGN PATENT DOCUMENTS

| | | |
|---|---|---|
| DE | 3915926 A1 | 2/1990 |
| DE | 4137426 C1 | 2/1993 |
| DE | 4132687 A1 | 4/1993 |
| DE | 19905840 C2 | 3/2001 |
| EP | 0664101 A1 | 7/1995 |
| WO | WO91/12044 | 2/1991 |

* cited by examiner

*Primary Examiner*—John Mulcahy
*Assistant Examiner*—Jocelyn Ram
(74) *Attorney, Agent, or Firm*—St. Onge Steward Johnston & Reens LLC

(57) ABSTRACT

The invention relates to a device for introducing an intubation tube into the trachea. The inventive device comprises a shaft, a receiving element arranged at the distal end of said shaft to which a proximal end of an intubation tube can be mounted and a coupling arranged at the proximal end of the shaft for coupling an endoscope thereto.

24 Claims, 5 Drawing Sheets

APPARATUS FOR INTRODUCING AN INTUBATION TUBE INTO THE TRACHEA

CROSSREFERENCE OF PENDING APPLICATION

This application is a continuation of pending international application PCT/EP00/01138 filed on Feb. 11, 2000 and designating US.

BACKGROUND OF THE INVENTION

The invention relates to an apparatus for introducing an intubation tube into the trachea.

The introduction of an intubation tube into the trachea is a very difficult procedure, which is very difficult to perform especially for children and when malformities are present. An intubation tube normally consists of a tube made of plastic or synthetic material, which after having been introduced into the trachea is held fixed at the end with the aid of an inflatable balloon to close off the remaining free volume of the trachea. The tube must be passed under the epiglottis and through the vocal chords. This area is only visible to a limited extent from the outside. This procedure is very difficult to perform, especially for small children and must be carried out with great care in order not to damage the mentioned body parts.

Particularly in emergencies, the tube must sometimes be placed very rapidly to allow an oxygen supply as soon as possible. The intubation in emergencies, for example with burns or poisoning of small children, must be carried out when the child is conscious, where strong resistance normally occurs.

A need for an apparatus therefore exists with which such a tube can be rapidly, precisely and reliably introduced into the trachea. It is also desirable to have the distal end of the tube constantly in view during the introduction procedure or to visually observe the insertion of this end.

It is therefore object of the present invention to provide an apparatus for introducing an intubation tube into the trachea, which allows a surgeon to insert the intubation tube in a most atraumatic manner.

SUMMARY OF THE INVENTION

The object is achieved according to the present invention with an apparatus comprising a shaft having a receptor arranged at the distal end of the shaft to which a proximal end of the intubation tube can be attached and with a coupler arranged at the proximal end of the shaft for coupling to an endoscope, a length of said shaft being variable.

The intubation tube can be reliably and securely attached to the apparatus by providing a receptor at the distal end of the shaft. This procedure can already be prepared before the actual operation, i.e. depending on the age and the size of the patient, a correspondingly suitable intubation tube can be attached to the apparatus. Normal lengths of the intubation tubes range from about 12 cm for small children to about 35 cm for adults. The provision of a coupler for attachment to an endoscope at the proximal end allows attachment of an optical instrument directly to the apparatus through which the introduction procedure can continuously be observed visually. The endoscope can be coupled so as to be an integral part of the apparatus and therefore be fixed and non-releasable.

In this case, the length of the apparatus, the length of the intubation tube and the length of the endoscope shaft are adapted to one another such that the distal end of endoscope lies precisely in the region of the distal end of the intubation tube. Both the intubation tube and the endoscope can be attached fixedly however releasably to the apparatus, so that the assembly of the three components represents a compact and narrow structure, which is simple to manipulate by the operator and at the same time provides the operator with the possibility of visually observing the introduction. The endoscope can be rigid, semi-flexible or also flexible.

After placement of the intubation tube, the endoscope can be decoupled and removed and the apparatus can also be released from the proximal end of the intubation tube, so that it can then be connected to the corresponding resuscitation devices or the like. In this configuration, the apparatus is particularly suited to be used for operative procedures by which the optimal length and sizes of the intubation tube and endoscope can be made available beforehand.

Since the length of the shaft is variable, adjustments can be made to the varying conditions during use of the same apparatus. Due to the change in length of the shaft, the connected endoscope can be achieved, i.e. in particular, the endoscope can be positioned in the region of the distal end of the repiratory tube, namely independent of the length of the intubation tube. In other words, a single such apparatus with a shaft changeable in length can be employed for different lengths of the intubation tubes, so that several apparatus need not be made available, each designed for a certain length of the intubation tube or for certain endoscopes.

This is especially helpful in emergencies, where for example only a certain intubation tube is available and correspondingly one certain endoscope, so that due to the variation in the length of the shaft, the optimal observation position for the introduction procedure can be achieved.

When anatomical anomalies are present, the endoscope can be moved back and forth due to the length variation of the shaft to achieve optimal observation conditions, so that the intubation tube can be introduced into the trachea rapidly and without trauma when such anomalies are present.

In a further embodiment of the invention, the shaft is configured to be telescopic. This configuration has the advantage that the shaft represents a narrow component despite the variability in length and that the storage space for the apparatus is relatively small. When not used, the shaft can be telescopically retracted.

In a further embodiment, the shaft is tubular. The feature has the advantage that the shaft of the endoscope can be inserted through the shaft and is surrounded by same from all sides and therefore protected. The tubular configuration of the shaft makes it possible to pass further instruments or optionally also other media such as gases or fluids through the shaft.

In a further embodiment of the invention, the shaft is configured with several telescopic tubes slideable within one another. The feature simplifies the length variability of the shaft in a constructively simple manner and at the same time the configuration as a tube allows the passage or introduction of instruments or media.

In a further embodiment of the invention, a gas connection is arranged at the proximal end of the apparatus, which communicates with the interior of the hollow shaft. The feature has the considerable advantage that live-saving oxygen can be supplied even when introducing the intubation tube, which can be decisive in saving life, especially in emergencies. In emergencies where suffocation is threatening, the operator when introducing the intubation tube is already capable of simultaneously introducing oxygen and need not wait until the tube has been placed before connecting the oxygen.

In a further embodiment of the invention, a handle is arranged at the distal end of the apparatus through which the apparatus can be manipulated. The feature has the considerable advantage that the operator can securely and fixedly hold and guide the apparatus in one hand when introducing the intubation tube with the handle, so that his other hand is free for other manipulations.

In a further embodiment of the invention, the receptor at the distal end of the shaft of the apparatus for attaching the intubation tube is configured as a muff, onto which the end of the intubation tube can be slid. The feature has the advantage that the intubation tube can be placed on the apparatus in a simple sliding procedure and correspondingly, after placement of the intubation tube, the connection can be released again.

In a further embodiment of the apparatus, the receptor is configured as a hollow muff, into which a proximal end of the intubation tube can be inserted. The feature has the advantage that a radially thin construction is achieved by the introduction of the intubation tube into the hollow muff.

In a further embodiment of the invention, the muff is configured to be slightly conical. The feature has the advantage that the intubation tube is seated fixedly in the receptor, however is still releaseable, and that a sufficient sealing surface is provided by the conical surfaces lying upon one another, so that the escape of gas being passed through the apparatus and the intubation tube is prevented.

In a further embodiment of the invention, the shaft is configured such that the endoscope shaft can be passed through the apparatus from the proximal end. The feature has the advantage that the endoscope can be introduced into the apparatus by a simple shifting procedure and the sensitive endoscope shaft is surrounded and protected by the shaft of the apparatus, so that in the end, only the optical end of the endoscope coupled thereto projects from the proximal end of the apparatus. Preferably, semi-flexible endoscopes are employed, i.e. those with an endoscope shaft capable of following the position and curvatures taken on by the intubation tube when being introduced into the trachea.

In a further embodiment of the invention, the shaft is configured such that a gas can be passed through the shaft, also when the endoscope is inserted. The feature has the advantage of multi-functionality, such that a respiratory gas can still be introduced through the shaft despite the fact that the endoscope is inserted.

In a further embodiment, the apparatus is provided with a slot along its length, through which the apparatus can be coupled to a shaft of an endoscope. The feature is of special advantage when the apparatus is to be attached to a rigid endoscope, whose shaft is bent at the distal end, a so-called intubation fiberscope. By providing the slot, the apparatus can be drawn in a radial movement onto the straight portion of the endoscope shaft, i.e. after the distal bend of the shaft, and then slid in direction of the proximal end and coupled to the endoscope. Rotary elements can be provided, which are rotated over the slot after attaching the apparatus to the endoscope shaft and thus prevent the apparatus from releasing to the side.

In a further embodiment, the apparatus can be clamped to the endoscope housing by the coupler. This very simple construction has the advantage that the apparatus can be secured to an existing conventional endoscope without any special adaptation of the endoscope in the region of the endoscope housing. To improve the clamping effect, a screw can be provided.

In a further embodiment of the invention, the coupler is configured as a locking mechanism for locking the apparatus to the endoscope or can be secured to the endoscope housing with a union nut connection.

When a locking mechanism is provided for locking the apparatus to the endoscope, it is preferred that the locking mechanism comprises at least one ball catch and at least one recess is formed in the endoscope housing for engaging the ball catch. The securement of the apparatus with a ball catch engaging in a recess on the endoscope has the particular advantage that the apparatus can be rapidly and securely fixed to the endoscope and released again just as rapidly.

It is also preferred that the recess be formed as a circumferential groove on the endoscope. The feature has the advantage that when attaching the apparatus to the endoscope, care need not be taken to provide a certain rotary orientation of the apparatus with respect to the axis of the endoscope, because the apparatus in this embodiment can be secured in any angular position with respect to the endoscope axis.

In a further embodiment, the securement of the apparatus to the endoscope housing is configured as a bayonet connection. In another embodiment of the invention, the coupler is configured to be integral with the endoscope. The feature has the advantage that the apparatus is fixedly coupled to the endoscope.

In a further embodiment of the invention, the endoscope is provided with a camera. The feature has the advantage that the operator can observe the image with both eyes and recognize the complicated anatomy and optionally anomalies and can react correspondingly so that the tube can be properly inserted and placed without trauma as far as possible.

It will be understood that the above-mentioned features and those to be discussed below are not only applicable in the given combinations, but may also be used in other combinations or taken alone without departing from the scope of the present invention.

BRIEF DESCRIPTION OF THE DRAWINGS

Embodiments of the invention are described in more detail in the following in conjunction with the drawings.

DETAILED DESCRIPTION OF PREFERRED EMBODIMENTS

An apparatus according to the invention is shown in the drawings and indicated on the whole with the numeral 10. As can be taken from the cross-sectional view of FIG. 1, the apparatus 10 comprises a central shaft 12 having a receptor 16 arranged at its distal end 14.

Figure 2:
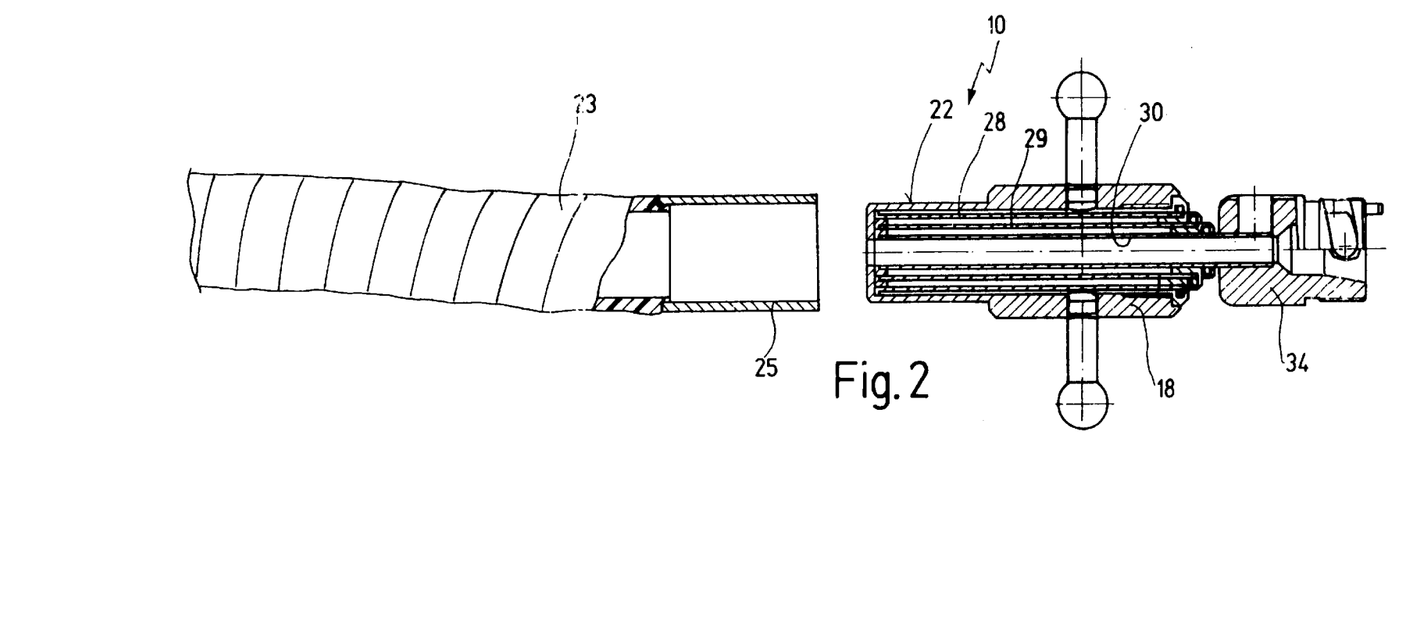
FIG. 2 shows a cross-sectional view corresponding to FIG. 1 in the completely retracted condition of the apparatus, where a section of the intubation tube is shown, which is slidable onto a receptor.

The receptor 16 has an approximately hollow tubular housing 18, where a hollow cylindrical muff 20 projects from its distal end. The outer side 22 of the muff 20 serves for pass-fitting a proximal end piece 25 of the intubation tube 23, as best seen in the illustration of FIG. 2. The muff 20 and the proximal end piece 25 are slightly conical, whereby the intubation tube 23 fixedly and sealingly can be seated on the muff 20.

The intubation tube 23 consists of a tube of synthetic material, as is known per se, and has a length of about up to 12 cm for intubation of small children and up to about 35 cm for intubation of adults.

Figure 1:
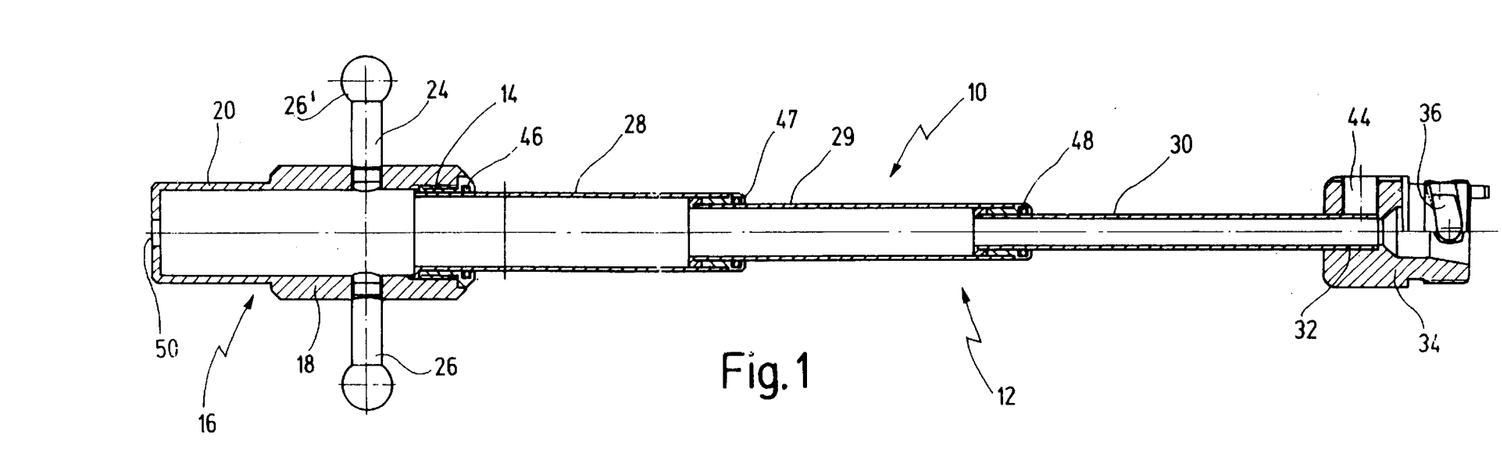
FIG. 1 shows a longitudinal cross-section of a first embodiment of an apparatus according to the present invention with a variable-length shaft in the form of three telescope tubes in the completely extended condition.

As can be seen in FIGS. 1 and 2, two rods 26, 26' extend radially opposed from one another from the outer side of the housing 18 and have a ball-shaped end, where these rods 26, 26' serve as a handle 24 for the apparatus 10.

The shaft 12 consists of three tubes 28, 29, 30 arranged telescopically to be shiftable within one another. The tube 28 of largest diameter is connected to be slidable but non-releasable at its distal end to the housing 18. The tube 29 is placed in the tube 28, which in turn has the tube 30 placed therein.

O-rings 46, 47, 48 provide an airtight, but telescopic-like shifting movement of the tubes 28, 29, 30 with respect to one another. It is also possible to attach the tube with the smallest diameter to the housing and to slide the other tubes telescopically thereon.

The proximal end of the shaft 12, in the present embodiment the proximal end of the tube 30, is connected to a coupler 34. The coupler 34, as seen in the cross-sectional view of FIGS. 1 and 2, comprises a bayonet guide 36. The bayonet guide is provided to guide a locking ring 38, not shown in FIGS. 1 and 2, as can be taken from FIGS. 3, 5, and 6. A pin 40 projects radially for rotating the ring 38, as will be described in more detail below.

Figure 3:
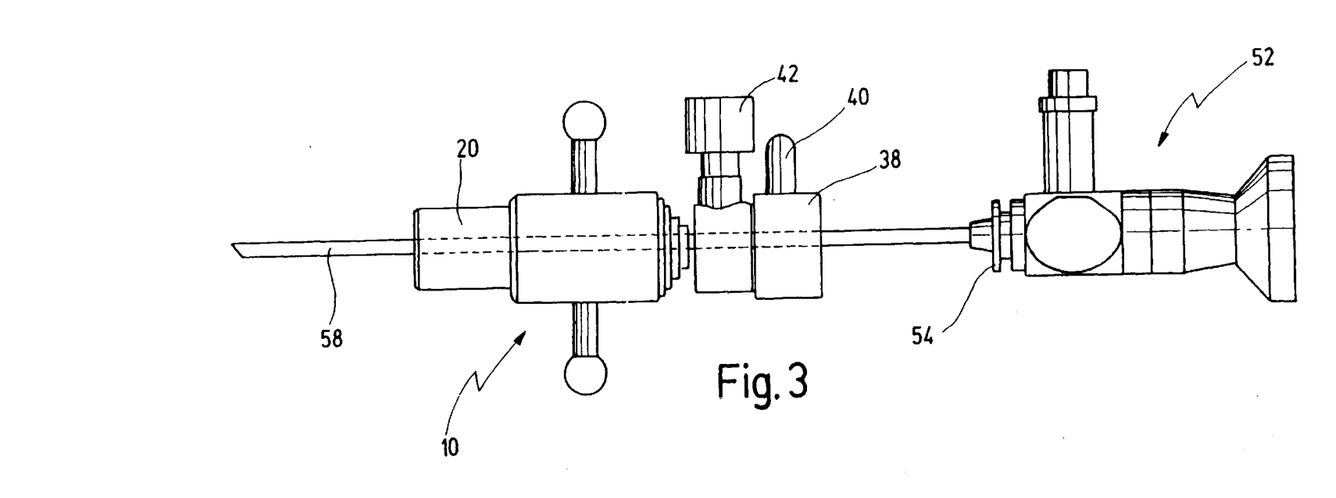
FIG. 3 shows a side view of the apparatus of FIG. 2 in retracted condition with a proximal coupler, where an endoscope is being introduced from the proximal end into the apparatus.
Figure 4:
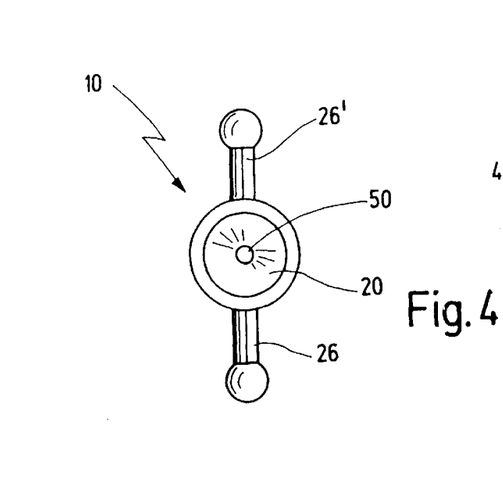
FIG. 4 shows an end face view of the apparatus from the distal end.
Figure 5:
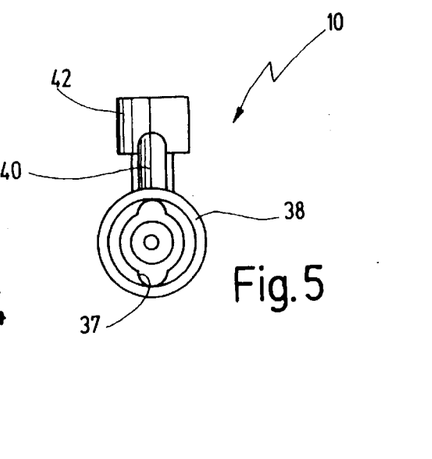
FIG. 5 shows an end face view of the apparatus from the proximal end.
Figure 6:
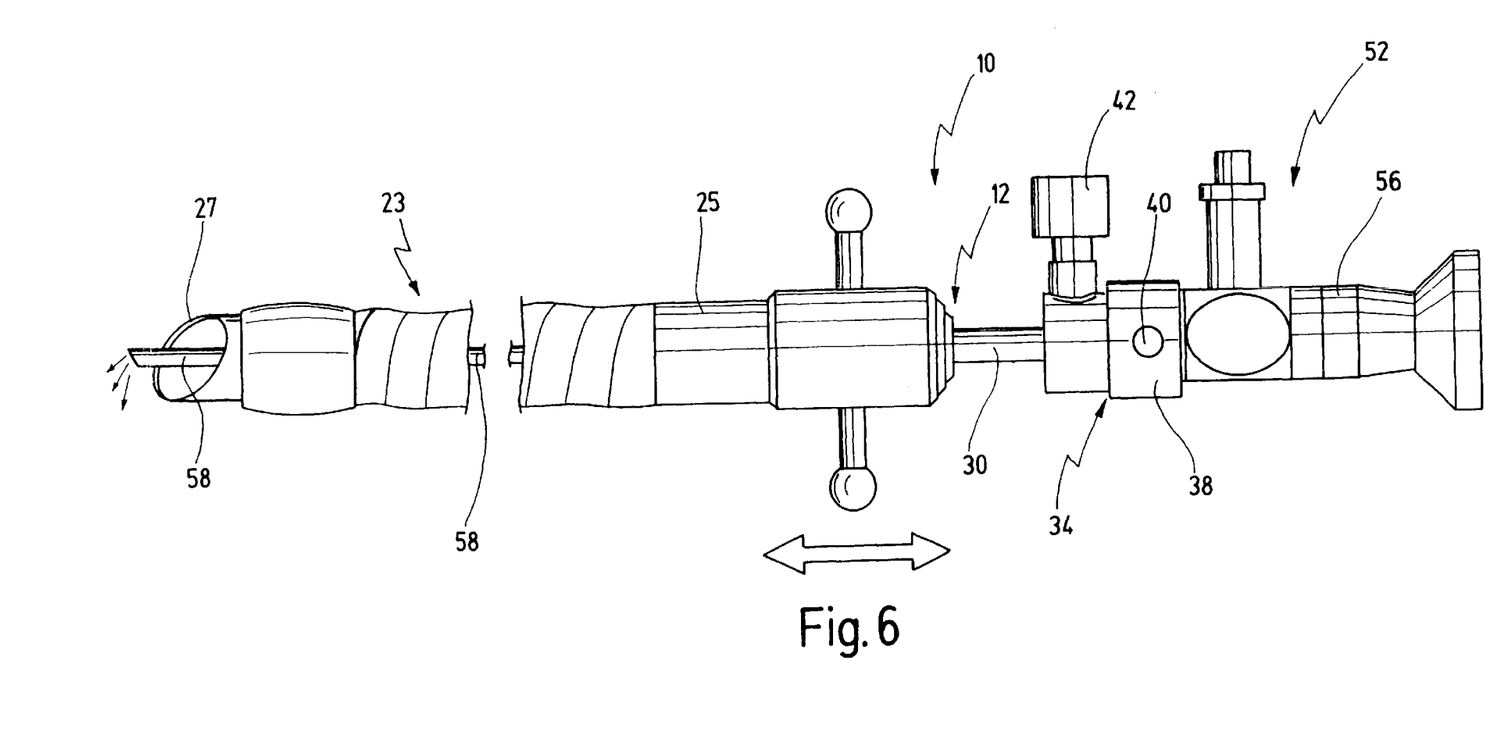
FIG. 6 shows an assembly of the apparatus, an endoscope and an intubation tube.

As can be taken from the cross-sectional view of FIG. 1, the interior of the tube 30 communicates with the exterior through a side channel 44. A gas connector 42 is mounted on this side channel 44 as can be seen in FIGS. 3, 5 and 6. It is also possible to pass a gas, for example oxygen, via the gas connector 42 from the proximal to the distal end of the apparatus 10, where the gas then exits at the distal end of the muff 20 through an opening 50, or when the intubation tube 23 is applied, the gas is passed into the intubation tube 23.

FIG. 1 shows the shaft 12 with its maximal length, i.e. the three tubes 28, 29, and 30 are extended telescopically to their maximum length. FIG. 2 shows the shaft 12 or the tubes 28, 29, 30 in the maximum retracted condition. The difference in lengths between FIGS. 1 and 2 therefore represents a measure of the variability in length of the shaft 12 for the apparatus 10. FIG. 3 illustrates how an endoscope 52 is inserted through the apparatus 10 from the proximal end. The endoscope 52 is shifted until its coupling piece 54 passes through the keyhole-like opening 37 of the coupler 34 shown in the side view of FIG. 5, which has a contour corresponding to the coupling piece 54. By rotating the locking ring 38 with the pin 40, the completely inserted endoscope 52 is locked to the coupler 34 or the apparatus 10.

This condition is shown in FIG. 6, i.e. the locking ring 38 has been rotated by 90° compared to the position in FIG. 3 to accomplish the locked condition. As can also be seen in FIG. 6, an intubation tube 23 has been slid onto the distal end of the apparatus 10.

The length of the endoscope 52 is selected such that its distal end lies in the region of the distal end 27 of the intubation tube 23. It is therefore possible to visually observe the respective position or introduction condition of the distal end 27 of the intubation tube 23 through the endoscope 52. The distal end of the endoscope 52 can now be placed at a relative position with respect to the distal end of the intubation tube 23, by a extending and retracting the telescopic tubes 28, 29, 30, where the respective optimal viewing conditions are present.

In addition, it is possible to employ intubation tubes of different lengths with the same apparatus 10, where with a given length of the endoscope, the length of the shaft is correspondingly adjusted by extending or extracting the tubes 28, 29, 30. For example, an endoscope with a shaft diameter of 2 mm and a tube having an outer diameter of 5 mm is employed for small children or infants.

The assembly shown in FIG. 6 is used to accomplish the introduction of the intubation tube 23, i.e. the intubation 23 is fixedly seated on the muff 20 and an endoscope 52 is coupled to the apparatus. This assembly is passed beneath epiglottis and through the vocal chords. The tongue of the patient is fixed by a laryngoscope spatula. Depending on whether a rigid, semi-flexible or flexible endoscope is employed, its shaft more or less strongly follows the curvature of the intubation tube. The shaft of a semi-flexible endoscope can be bent by about ±30°, depending on the anatomical conditions of the trachea. For known anomalies, correspondingly curved endoscopes can be employed.

Finally, the tube is released and completely inserted in the trachea, brought up to the branching of the air passages and fixed there, normally with an inflatable balloon provided at the distal end of the intubation tube 30. To release the intubation tube 23, one or two fingers of the hand holding the assembly with the handle 24 can push the proximal end piece 25 of the intubation tube 23 away from the muff 20. The assembly of the apparatus 10 and the endoscope 52 can still be used for purposes of observation. The apparatus 10 is then removed again with the endoscope 52.

The apparatus 10 thus serves as a fixing means both for the intubation tube and for the observation optics and represents a simple compact unit for introducing an intubation tube.

If oxygen or respiration air is to be supplied during introduction, this can be accomplished through the gas connection arranged at the side.

As shown in FIG. 6 with the double arrow, the variability in length of the shaft allows an optimal adaptation to the condition of the patient, so that a rapid, reliable and non-traumatic introduction is possible even for difficultly accessible trachea, for example where malformities are present or for small children.

Should an image be displayed on a video monitor instead of a direct observation through the endoscope, a camera can be additionally provided or the endoscope can be provided with an integrated camera, i.e. configured as a video endoscope. Anatomical anomalies can be precisely observed by enlarging the video image. This is very helpful, especially when intubating newborn babies or infants. The operator sees the optionally enlarged video image in his view, so that he can clearly recognize difficult anatomies and possibly anomalies and can properly insert the intubation tube despite these difficulties.

Figure 7:
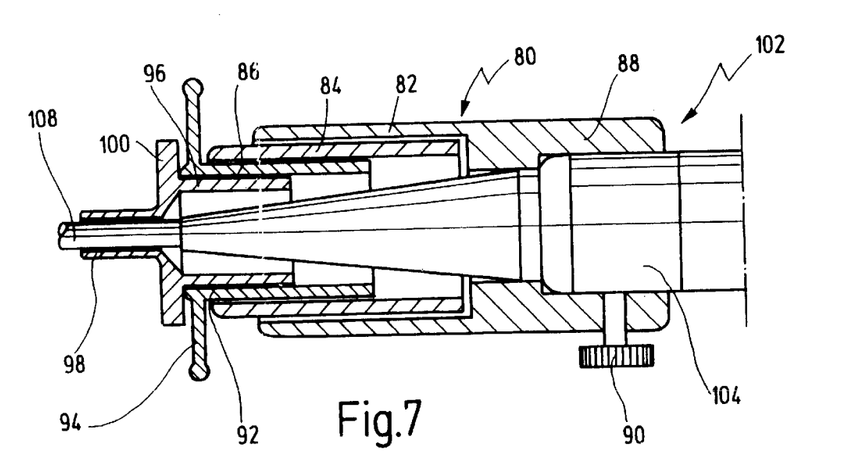
FIG. 7 shows a longitudinal cross-section of an apparatus which can be coupled to the endoscope with an adjustment screw.
Figure 8:
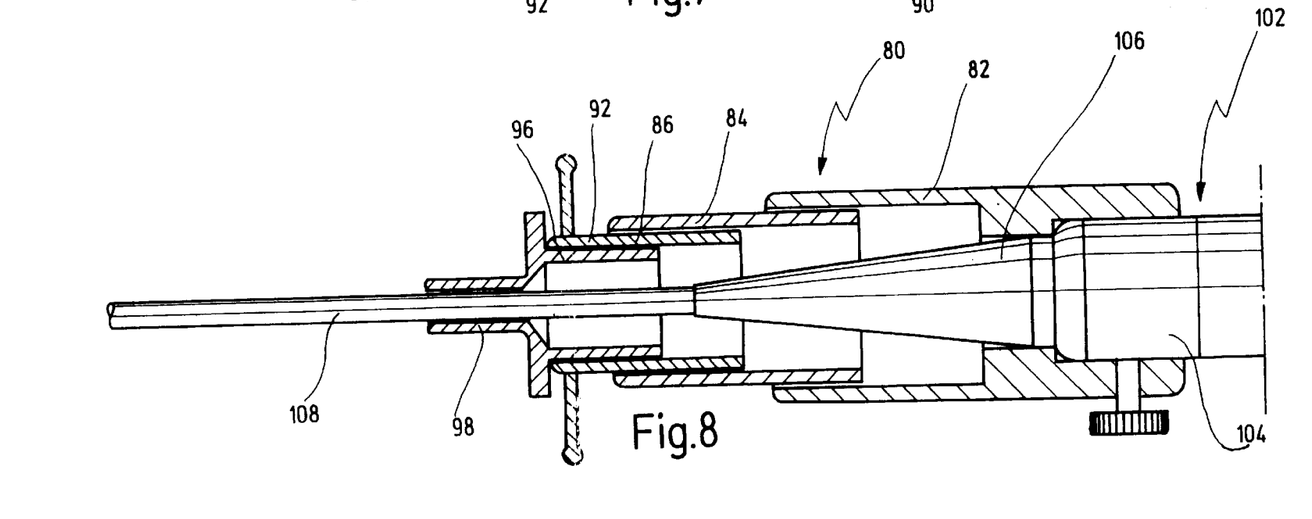
FIG. 8 shows the apparatus of claim 7 in a further extended telescopic condition.

FIGS. 7 and 8 show a further embodiment of an apparatus 80 coupled to an endoscope 102. The endoscope 102 is a flexible endoscope. The apparatus 80 is also configured to be variable in length and for this purpose has a tubular extension 82 at its distal end into which a tube 84 is inserted. A further tube 86 is inserted in this tube 84. These three tubes are retracted into one another in telescopic manner in FIG. 7.

A coupler 88 for connecting the endoscope 102 is configured as a tube projection at the proximal end, which can be shifted onto a corresponding portion of the optical head 104 of the endoscope 102. The apparatus 80 can be fixed to the endoscope 102 by a radially extending adjustment screw 90.

The optical head 104 of the endoscope 102 extends with a conically tapered portion 106 to an elongate shaft 108. The conically tapered portion 106 extends through the interior of the tubes 84, 86 retracted within one another. The interior surface 92 of the innermost tube 86 acts as a receptor for an intubation tube 98, namely for its proximal end 96.

The outer diameter of the proximal end 96 is selected such that it can be inserted in pass fit into the receptor 92. The receptor 92 and the proximal end portion 96 can be conical to provide a fixed, secure seating.

A ring flange 100 provides a stop for the introduction depth of the intubation tube 98 into the receptor 92. A radially extending handle 94 projects from the innermost tube 86, which not only allows handling of the apparatus 80 when being coupled to the endoscope 102, but also serves to shift the telescopically arranged tubes 84, 86. An axially extended condition is shown in FIG. 8.

Figure 9:
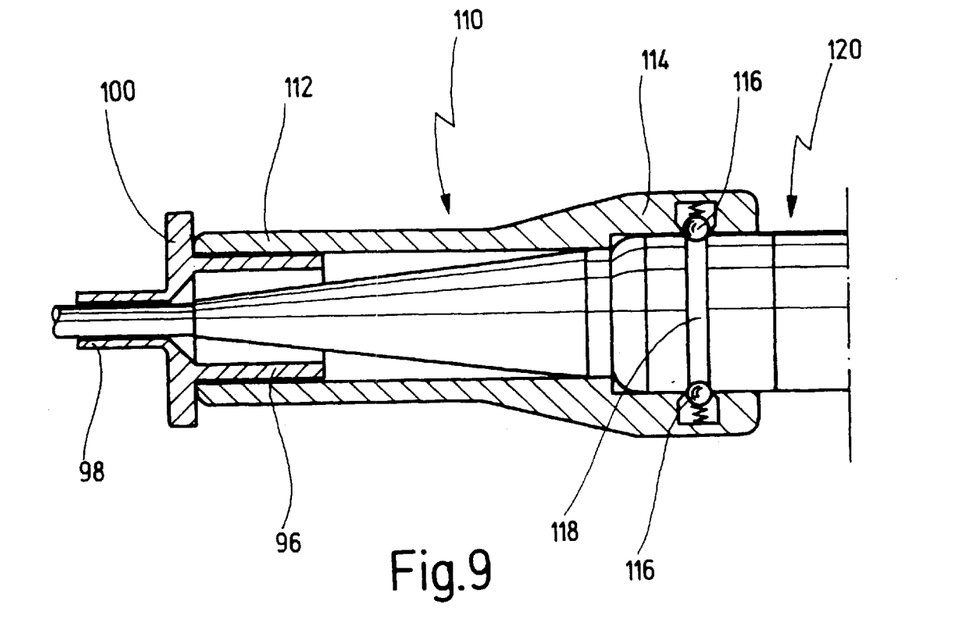
FIG. 9 shows a longitudinal cross-section of a further embodiment of an apparatus having a coupler with a ball catch.

A further embodiment of the apparatus 110 of the present invention is shown in FIG. 9, where the coupler 114 for connection to the endoscope 120 comprises a ball catch mechanism 116. A groove 118 is cut into the outer surface of the endoscope 120 for this purpose, into which the correspoonding spring biased ball, held at the inner side of the coupler 114, can catch when the apparatus 110 is slid onto the endoscope 120. A receptor 112 in the form of a tubular or hollow muff is provided at the opposing end of the coupler 114 into which the above-mentioned proximal portion 96 of the intubation tube 98 can be inserted. This intubation tube 98 can be configured to be identical to that described in conjunction with FIGS. 7 and 8, so that the reference numerals have not been changed.

Figure 10:
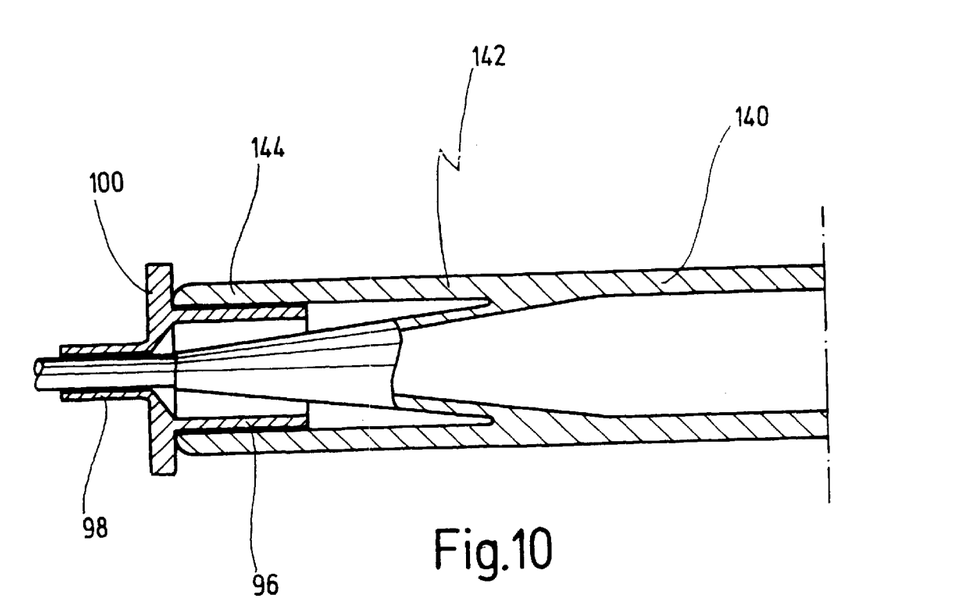
FIG. 10 shows a cross-sectional view of a further embodiment of an apparatus according to the present invention, which is integrally coupled to an endoscope.

FIG. 10 shows a further embodiment of the apparatus 144 according to the present invention, which is fixedly connected to the endoscope 140 by stays 142. The stay 142 thus provides the connection for a fixed and non-releasable coupling in this case of the apparatus 144 to the endoscope 140.

The receptor for the intubation tube 98 is again configured as a tubular end of the apparatus 144, into which the proximal end portion 96 of the intubation tube 80 is inserted. The corresponding surfaces can also be configured to be slightly conical in this case.

What is claimed is:

1. An apparatus for introducing an intubation tube into a trachea, comprising:
    a shaft having,
    a plurality of interlocked sections, each having an interlocking stop for inhibiting the sections from being separated from one another,
    a first coupler arranged at a distal end of said shaft, said first coupler provided for coupling to an intubation tube; and
    a second coupler arranged at a proximal end of said shaft for coupling to an endoscope, and
    wherein a length of said shaft is variable such that the intubation tube and the endoscope are axially movable relative to each other.

2. The apparatus of claim 1, wherein said shaft is configured to be telescopic.

3. The apparatus of claim 1, wherein said shaft is tubular.

4. The apparatus of claim 3, wherein said shaft is configured of several telescopic tubes shiftable within one another.

5. The apparatus of claim 1, wherein a gas connector is arranged at said proximal end of said shaft, which gas connector communicating with an interior of said shaft.

6. The apparatus of claim 1, wherein a handle is arranged at said distal end of said shaft, through which handle said apparatus can be handled.

7. The apparatus of claim 1, wherein said first coupler is configured as a tube, onto which a proximal end of said intubation tube can be slid.

8. The apparatus of claim 7, wherein said tube is configured to be slightly conical.

9. The apparatus of claim 1, wherein said first coupler is configured as a hollow tube into which hollow tube a proximal end of said intubation tube can be inserted.

10. The apparatus of claim 9, wherein the hollow tube is configured to be slightly conical.

11. The apparatus of claim 1, wherein said shaft is configured hollow allowing to pass a shaft of an endoscope through said apparatus from a proximal end thereof.

12. The apparatus of claim 1, wherein said shaft is configured such that a gas can be passed through said shaft, also when an endoscope is inserted into said shaft.

13. The apparatus of claim 1, wherein a slot is provided over an entire length of said apparatus in order to place said apparatus laterally onto a shaft of an endoscope.

14. The apparatus of claim 1, wherein said second coupler is designed to fixedly attach the shaft to an endoscope attached to said second coupler.

15. The apparatus of claim 1, wherein said second coupler comprises a locking mechanism for locking said second coupler to an endoscope.

16. The apparatus of claim 15, wherein said locking mechanism comprises at least one ball catch, and wherein said endoscope is configured with at least one recess engaging with said ball catch.

17. The apparatus of claim 16, wherein said recess for engaging with said ball catch is formed as a circumferential groove.

18. The apparatus of claim 1, wherein said second coupler is designed with a union nut connection for connecting said second coupler to said endoscope.

19. The apparatus of claim 1, wherein said second coupler is designed as a bayonet for connecting to said endoscope having a respective bayonet.

20. The apparatus of claim 1, having an intubation tube attached to said distal end of said shaft and being coupled to an endoscope at a proximal end of said shaft.

21. The apparatus of claim 1, wherein said shaft is integrally formed with an endoscope.

22. The apparatus of claim 1, wherein said endoscope for coupling to said second coupler having a shaft selected from the group consisting of rigid shafts, semi-flexible shafts and flexible shafts.

23. The apparatus of claim 22, wherein said endoscope is provided with a camera.

24. A coupling apparatus for introducing an intubation tube into a trachea, comprising:
   an intubation tube;
   an endoscope;
   a shaft member of variable length, having a proximal and a distal end;
   a first coupler, provided at the distal end of the shaft member, for connecting the shaft member to the intubation tube; and
   a second coupler, provided at the proximal end of the shaft member, for connecting the shaft member to the endoscope, such that the endoscope extends through the shaft member and into the intubation tube;
   wherein the shaft member of variable length has a plurality of slideable shaft sections, each section having an interlocking stop for inhibiting the sections from being separated from one another such that the endoscope is adjustable between a maximum insertion position when the shaft is fully compressed and a minimum insertion position when the shaft is fully extended.

* * * * *